United States Patent [19]

Dodd

[11] 4,228,311
[45] Oct. 14, 1980

[54] SELECTIVE DEALKYLATION OF 4-TERTIARY-ALKYL-2,5-XYLENOL

[75] Inventor: John R. Dodd, Ponca City, Okla.

[73] Assignee: Conoco, Inc., Ponca City, Okla.

[21] Appl. No.: 47,190

[22] Filed: Jun. 8, 1979

[51] Int. Cl.$^2$ .................. C07C 39/06; C07C 37/22
[52] U.S. Cl. ................................. 568/805; 568/751; 568/788
[58] Field of Search ................ 568/805, 751, 788

[56] References Cited

U.S. PATENT DOCUMENTS

| | | | |
|---|---|---|---|
| 2,435,087 | 1/1948 | Luten et al. | 568/750 |
| 2,497,971 | 2/1950 | Basterfield | 568/750 |
| 2,603,662 | 7/1952 | Stevens | 568/805 |
| 2,802,884 | 8/1957 | D'Alelio | 568/788 |
| 2,917,487 | 12/1959 | Jones et al. | 568/750 |

FOREIGN PATENT DOCUMENTS

| | | | |
|---|---|---|---|
| 1153027 | 8/1963 | Fed. Rep. of Germany | |
| 43-22968 | 3/1968 | Japan | 568/805 |
| 582057 | 11/1946 | United Kingdom | 568/750 |
| 706107 | 3/1954 | Japan | 568/805 |

*Primary Examiner*—Werren B. Lone
*Attorney, Agent, or Firm*—Cortlan R. Schupbach, Jr.

[57] ABSTRACT

A method is described for the selective dealkylation of 4-tertiary-alkyl-2,5-xylenol while it is admixed with 6-tertiary-alkyl-2,4-xylenol by contacting the mixture of alkylated xylenols with a polymer-bound sulfonic acid catalyst at temperatures of 60° C. or less and pressures of from about 0.5 to 5 atmospheres. The method is useful in separating 2,4-/2,5-xylenol mixtures.

9 Claims, No Drawings

SELECTIVE DEALKYLATION OF 4-TERTIARY-ALKYL-2,5-XYLENOL

This invention relates to a method for the selective dealkylation of 4-tertiary-alkyl-2,5-xylenol while admixed with 6-tertiary-alkyl-2,4-xylenol. More specifically, this invention relates to a method for such dealkylation by contacting the mixture with a polymer-bound sulfonic acid catalyst at a temperature of or less than 60° C. and pressures from about 0.5 to about 5 atmospheres. This selective dealkylation is useful for the separation of 2,4-/2,5-xylenol mixtures.

For many applications it is desirable to separate admixtures of 2,4- and 2,5-xylenol into the individual isomers such that each is available in high purity. These materials cannot be separated by fractional distillation since these isomers boil within 0.1° C. of one another. Consequently, other methods of achieving this separation must be utilized. The instant invention, as well as providing a method for selectively dealkylating t-alkylated 2,5-xylenol from t-alkylated 2,4-xylenol, provides a method for the separation of 2,5-xylenol from 2,4-xylenol starting from a mixture of these isomers using the selective dealkylation described herein. The key step in such a separation is the selective dealkylation of 4-tertiary-alkyl-2,5-xylenol in the presence of 6-tertiary-alkyl-2,4-xylenol using a polymer-bound sulfonic acid catalyst and a temperature of 60° C. or less and preferably 50° C. or less.

The art contains many references relating to phenolic alkylations and dealkylations. The use of polymer-bound sulfonic acid catalysts for alkylation and dealkylation is known. U.S. Pat. No. 2,802,884 describes the use of a sulfonic acid catalyst on a resin matrix as an alkylation/dealkylation catalyst at temperatures greater than or equal to 100° C. Isomer separation is not taught.

Processes for the separation and purification of 2,4-xylenol and 2,5-xylenol from their admixture are known. Representative, but not exhaustive, of the prior art is British Patent 582,057, which describes a method for separating 2,4-xylenol and 2,5-xylenol involving the butylation of a 2,4-/2,5-xylenol mixture, then treating the butylated mixture with an aqueous alkali solution to form insoluble 6-t-butyl-2,4-xylenol and removing the solid. The remaining solution is then acidified to precipitate 4-t-butyl-2,5-xylenol. The two butylated xylenols, now separated, are each debutylated to afford purified 2,4-xylenol and 2,5-xylenol. British Pat. No. 706,107 teaches that use of a sulfuric acid catalyst alkylates only 2,4-xylenol with diisobutylene while 2,5-xylenol is unchanged. A base is used to extract unchanged 2,5-xylenol. U.S. Pat. No. 2,917,487 shows the separation of 2,4-/2,5-xylenols by selective resinification. German Pat. No. 1,153,027 teaches separation of 2,4-/2,5-xylenols by butylation with isobutylene, catalyzed by perchloric acid, and then separation of the isomeric butylated xylenols by fractional distillation. Desired individual isomers are then debutylated.

All of the above methods for the separation of 2,4-xylenol and 2,5-xylenol from their admixture require an aqueous treatment of the xylenols and/or alkylated xylenols either before, during, or after the isomer separation. In such an aqueous treatment, a considerable amount of the xylenols is frequently not recoverable. The water used for the aqueous treatment is contaminated with phenolic compounds, presenting a severe disposal problem. A method for the separation of 2,4-xylenol and 2,5-xylenol from their admixture which does not require any aqueous treatment whatsoever of the xylenol material would be of great benefit.

It is therefore an object of the instant invention to provide a method for the selective dealkylation of 4-t-alkyl-2,5-xylenol (t-alkylated 2,5-xylenol) from admixture with 6-t-alkyl-2,4-xylenol (t-alkylated 2,4-xylenol) under nonaqueous conditions. This method can be effectively utilized as the key step for the separation of 2,4-xylenol and 2,5-xylenol from admixture of the two xylenols. Other objects will become apparent to those skilled in this art as the description proceeds.

I have now discovered a method for selectively dealkylating 4-t-alkyl-2,5-xylenol while an admixture with 6-t-alkyl-2,4-xylenol comprising contacting the t-alkylated xylenol mixture with a polymer-bound sulfonic acid catalyst at temperatures of or less than 60° C. and pressures ranging from about 0.5 to about 5 atmospheres. This method is advantageously used for the recovery of high purity 2,5-xylenol from admixture with 2,4-xylenol by t-alkylating the entire 2,4-xylenol/2,5-xylenol mixture to form predominantly 4-t-alkyl-2,5-xylenol and 6-t-alkyl-2,4-xylenol. The resulting mixture is then fractionated to remove any unalkylated xylenols and obtain a mixture containing predominantly the above t-alkylated xylenols. The 4-t-alkyl-2,5-xylenol present in the latter mixture is then selectively dealkylated by the method of the instant invention and the resulting mixture is fractionated to separate and recover 2,5-xylenol in high purity.

If, in addition, it is desired to recover 2,4-xylenol in high purity, the 6-t-alkyl-2,4-xylenol is purified by fractionation and then debutylated over silica-alumina catalysts at temperatures of from about 200° C. to about 220° C. and at or near ambient pressure. The resulting product stream is fractionated to obtain 2,4-xylenol in high purity.

The alkylating agents useful in the instant invention are generally those which afford a tertiary alkyl group. Isobutylene (2-methyl-1-propene), 2-methyl-1-butene, 2-methyl-1-pentene, and 2-methyl-1-heptene are preferred. Isobutylene is most preferred and is used throughout the specification to illustrate the instant invention.

The selective dealkylation of the instant invention can be accomplished using a continuous tubular reactor packed with a polymer-bound sulfonic acid catalyst at suitable temperatures. 2,5-xylenol of high purity is obtained upon fractionation of the reactor effluent. This process for the separation of 2,4- and 2,5-xylenol mixtures is set forth in the schematic diagram presented below.

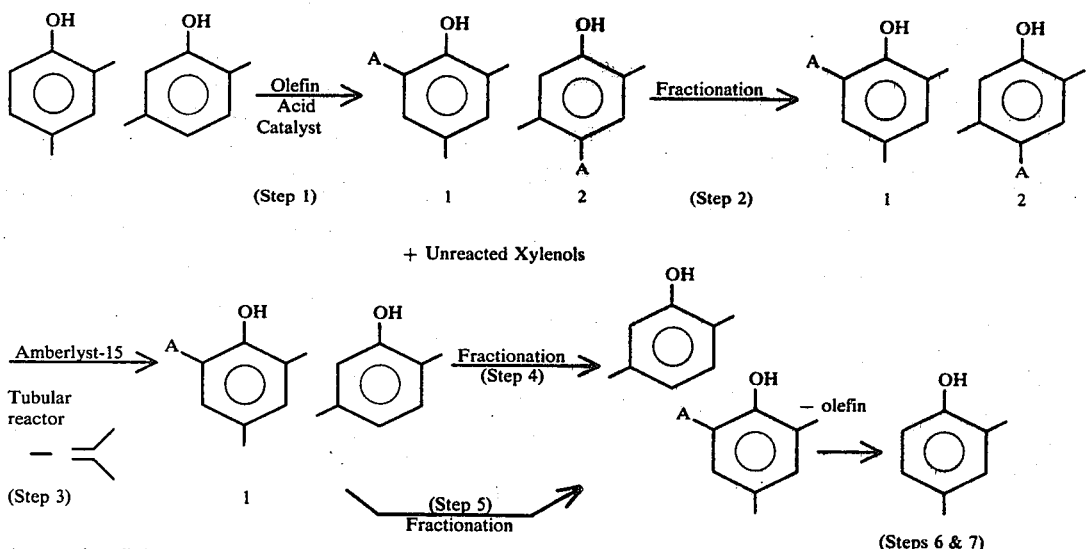

A = a tertiary alkyl group

Step 1 shown in the diagram (tertiary alkylation) is carried out at temperatures of from about 20° to about 100° C. and at pressures of from about ambient to about 200 pounds per square inch gauge. Either conventional acidic catalysts (e.g. sulfuric acid, boron trifluoride) or suitable polymer-supported acidic catalysts can be used for this step. A suitable polymer-supported acidic catalyst is used in cases where it is desired to have a process for separating 2,4-/2,5-xylenols which requires no aqueous treatment. The mole ratio of xylenol to olefin in this t-alkylation should be at least 1 to 0.8, respectively, but can be higher as desired.

The resulting mixture from the above t-alkylation is then fractionated (step 2) at approximately 10 to 60 millimeters (mercury pressure) in order to remove any unalkylated xylenols and to purify the t-alkylated xylenols, now comprising mainly 6-t-alkyl-2,4-xylenol and 4-t-alkyl-2,5-xylenol.

The mixture of 6-t-alkyl-2,4-xylenol and 4-t-alkyl 2,5-xylenol is then passed over a polymer-bound sulfonic acid catalyst (step 3) at temperature of from about 20° C. to about 60° C. and preferably from about 40° C. to about 50° C. This selective dealkylation is preferably carried out at atmospheric pressure, but any pressure in the range of about 0.5 to about 5.0 atmosphere can be used. Selective dealkylation is best accomplished in a continuous reactor containing polymer-bound sulfonic acid catalyst. Suitable liquid hourly space velocities (LHSV) for this reactor are from about 0.4 to about 2.5. Generally, any strongly acidic polymer-bound sulfonic acid catalyst that is stable under the above conditions is suitable. Preferred catalysts are strongly acidic sulfonated divinylbenzene-styrene copolymers containing at least about 2% crosslinking. The product stream from selective dealkylation is then fractionated (step 4) to separate 2,5-xylenol from the t-alkylated components and other components (primarily isobutylene and oligomers of isobutylene) and to obtain 2,5-xylenol in high purity.

Should 2,4-xylenol be desired in pure form, the mixture of t-alkylated components obtained as the higher boiling fraction in the step 4 fractional distillation is further fractionated (step 5) to separate 6-t-alkyl-2,4-xylenol from any remaining 4-t-alkyl-2,5-xylenol. Clearly, such fractionation could be carried out during the fractionation for 2,5-xylenol recovery. Purified 6-t-alkyl-2,4-xylenol is then debutylated (step 6) over a silica-alumina catalyst at about 200° to about 220° C. at about atmospheric pressure. The resulting 2,4-xylenol mixture is then fractionated (step 7) to obtain high purity 2,4-xylenol.

The instant invention has several advantages in the separation of 2,4-/2,5-xylenols when compared to other methods presently known to the art. The invention can be employed for the separation of 2,4-/2,5-xylenols under conditions requiring no aqueous treatment of the xylenol mixtures. Aqueous streams contaminated with phenolic compounds leading to losses of phenolic material with consequent disposal problems are avoided completely. The instant invention can be conducted either batchwise or continuously. The process is particularly well-suited for a completely continuous mode of operation utilizing continuous reactors for steps 1 and 3 and continuous distillation units for the fractionations. The 2,5-xylenol product obtained by the instant method contains less pentamethylbenzene than that obtained using many existing processes when the starting material is 2,4-/2,5-xylenol mixtures obtained from phenol methylation. This is important since some pentamethylbenzene (~0.3%) is typically formed during phenol methylation and upon fractionation becomes concentrated in the 2,4-/2,5-xylenol mixture. This pentamethylbenzene contaminant is removed in the instant invention during fractionation separating t-alkylated xylenols from unreacted xylenols. When isobutylene is the olefin used, the distillation required for the separation of 2,5-xylenol and 6-t-butyl-2,4-xylenol is much more easily accomplished (30° C. difference in boiling point) than the prior art separation of 6-t-butyl-2,4-xylenol and 4-t-butyl-2,5-xylenol (20° C. difference in boiling points).

The instant invention is more concretely described with reference to the examples below wherein all parts and percentages are by weight unless otherwise stated. The examples are provided to illustrate the instant invention and not to limit it.

EXAMPLE 1

A cresylic acid mixture containing 2,4-xylenol and 2,5-xylenol in addition to other phenolic components was used for the experiment. This mixture had the following composition:

| | |
|---|---|
| 19.05% | 2,3-xylenol |
| 34.69% | 2,4-/2,5-xylenols (composition = 48.75% 2,5-xylenol and 51.25% 2,4-xylenol |
| 9.88% | 2,6-xylenol |
| 29.31% | 2,4,6-trimethylphenol |
| 3.53% | 2,3,6-trimethylphenol |
| 2.89% | pentamethylbenzene and small amounts (0.5%) of phenol and cresols |

A feed consisting of 748 grams of the above cresylic acid mixture and 254 grams (4.54 moles) of isobutylene was passed through a stainless steel continuous tubular reactor (57 centimeters long × 1.30 centimeters inside diameter and having a catalyst volume of 66.4 ml) packed with 44 grams of a polymer-bound sulfonic acid catalyst (dry Amberlyst-15 ®, trademark of and sold by Rohm and Haas). The reactor was maintained at 38° C. and had a three psig backpressure. The feed mixture was pumped into the reactor at a rate of 0.94 milliliter (ml) per minute corresponding to a liquid hourly space velocity (LHSV) of 0.85. The first 93 grams of the product stream was collected as sample 1. The next 853 grams was collected as sample 2. GC analysis of sample 2 indicated the following composition:

| | |
|---|---|
| isobutylene | 0.10% |
| t-butanol | 0.38% |
| isobutylene oligomers | 9.52% |
| 2,6-xylenol | 0.76% |
| 2,4-/2,5-xylenol | 10.13% |
| 2,3-xylenol | 2.65% |
| 2,4,6-trimethylphenol | 22.78% |
| 2,3,6-trimethylphenol | 0.87% |
| pentamethylbenzene | 1.35% |
| 6-t-butyl-2,4-xylenol | 7.77% |
| 4-t-butyl-2,6-xylenol | 7.20% |
| 6-t-butyl-2,3-xylenol | 11.46% |
| 4-t-butyl-2,5-xylenol | 12.04% |
| 1-t-butoxy-4-t-butyl-2,5-xylene | 0.17% |
| 4-t-butyl-2,3,6-trimethylphenol | 1.33% |
| 4,6-di-t-butyl-2,3-xylenol | 8.55% | and several minor unidentified components totaling 3%. In Sample 2, 62.5% of the 2,4-/2,5-xylenol was butylated.

The above sample was fractionally distilled at 30 millimeters on a spinning band column to remove all unbutylated 2,4-/2,5-xylenol. The distillation cut between 122° and 180° C. was collected, and amounted to 422 grams. This sample contained no 2,4-/2,5-xylenols, 0.6% 2,3-xylenol, 16.79% 2,4,6-trimethylphenol, 0.44% 2,3,6-trimethylphenol, 0.48% pentamethylbenzene, 14.51% 6-t-butyl-2,4-xylenol, 13.8% 4-t-butyl-2,6-xylenol, 21.9% 6-t-butyl-2,3-xylenol, 23.98% 4-t-butyl-2,5-xylenol, 1.14% 4-t-butyl-2,3-xylenol, and 3.82%-4,6-di-t-butyl-2,3-xylenol.

The recovered sample was passed through the tubular reactor packed with polymer-bound sulfonic acid catalyst under the conditions set forth in Table 1. The product stream was collected in 20 milliliter fractions. The fractions were analyzed by gas chromatography. The reactor was operated under a given set of conditions until two successive fractions showed no differences in their gas chromatographic traces. These fractions were then taken as representative of the particular conditions used.

EXAMPLE 2

A 37.3 gram sample of the product stream from the reactor operated at 50° C. and 0.85 LHSV was fractionally distilled on a spinning band column at 30 millimeters of mercury. Distillation cuts enriched in 2,4-/2,5-xylenol were analyzed by gas chromatography using a 300 foot ditridecylphthalate capillary column to determine the relative amounts of 2,4-xylenol and 2,5-xylenol present. The results are shown in Table 1.

EXAMPLE 3

A 36.7 gram sample of product stream from the reactor operated at 60° C. and an LHSV of 1.04 was treated under the same conditions as set forth in Example 2. The 2,5-xylenol purities are likewise shown in Table 1.

TABLE 1
SELECTIVE DEBUTYLATION OF 4-t-BUTYL-2,5-XYLENOL

| Sample | T (°C.) | LHSV (Hr⁻¹) | Pressure (psig) | Cmpd 1 24M6B (% Conv.) | Cmpd 2 25M4B (% Conv.) | 2,5 Xylenol Purity (%) |
|---|---|---|---|---|---|---|
| 1 | 90 | 0.82 | 0 | 78 | 99 | — |
| 2 | 70 | 0.84 | 0 | 24 | 90 | — |
| 3 | 60 | 0.94 | 0 | 2.2 | 84 | 93 |
| 4 | 50 | 0.85 | 0 | 0 | 69 | 97 |

In the table, 24M6B is 6-t-butyl-2,4-xylenol, 25M4B is 4-t-butyl-2,5-xylenol. 2,5-xylenol purity is defined as the percentage of 2,5-xylenol in the 2,4-/2,5-xylenol mixture obtaned after steps 1 through 4, as determined by gas chromatographic analysis.

Thus the present invention provides a process for dealkylating 4-t-alkyl-2,5-xylenol in the presence of 6-t-alkyl-2,4-xylenol over a sulfonic acid catalyst on a polymer support at a suitable temperature. As set forth in Table 1, at temperatures above 50° C. significant amounts of 6-t-butyl-2,4-xylenol are also debutylated. However, up to 60° C., it is apparent that 2,5-xylenol of relatively high purity can be obtained using the instant invention. The preferred temperature range is thus below 50° C. for high purity and preferably 40° to 50° C., although 2,5-xylenol of relatively high purity can be obtained at temperatures up to 60° C. Thus, 2,5-xylenol of high purity can be obtained using the method of the instant invention when the reactor temperature of the debutylation step is carefully controlled.

While certain embodiments and details have been shown for the purpose of illustrating this invention, it will be apparent to those skilled in this art that various changes and modifications may be made herein without departing from the spirit or scope of the invention.

I claim:

1. An improved method for selectively dealkylating 4-t-alkyl-2,5-xylenol when in admixture with 6-t-alkyl-2,4-xylenol by contacting a mixture of the above components with a strongly acidic polymer-bound sulfonic acid catalyst, the improvement comprising carrying out the dealkylation at temperatures equal to or less than 60° C. and pressures of from about 0.5 to about 5 atmospheres.

2. A method as described in claim 1 wherein the olefin utilized to prepare the admixture of 4-t-alkyl-2,5-xylenol and 6-t-alkyl-2,4-xylenol, is one capable of providing a tertiary alkyl group and is selected from the group consisting of isobutylene, 2-methyl-1-butene, 2-methyl-1-pentene, and 2-methyl-1-heptene.

3. A method as described in claim 2 wherein isobutylene is the olefin.

4. A method as described in claim 1 wherein the temperature of debutylation is from about 25° C. to about 60° C.

5. A method as described in claim 1 wherein the remaining 6-t-butyl-2,4-xylenol is purified by fractionation, debutylated over a silica-alumina catalyst at temperatures of from about 200° to about 220° C., and then fractionated to recover 2,4-xylenol of high purity.

6. A method for the recovery of high purity 2,5-xylenol from admixture with 2,4-xylenol comprising
  (1) butylating the entire 2,4-xylenol/2,5-xylenol mixture with isobutylene at a temperature of from about 20° C. to about 100° C. and pressures of from about ambient to about 200 pounds per square inch gauge in the presence of an acid catalyst to form predominantly 4-t-butyl-2,5-xylenol and 6-t-butyl-2,4-xylenol,
  (2) fractionating the butylated mixture to remove any unbutylated xylenols and provide a mixture containing predominantly 4-t-butyl-2,5-xylenol and 6-t-butyl 2,4-xylenol.
  (3) selectively debutylating 4-t-butyl-2,5-xylenol while in admixture with 6-t-butyl-2,4-xylenol to afford a mixture containing predominantly 2,5-xylenol and 6-t-butyl-2,4-xylenol by
  (4) contacting the butylated mixture from (2) with a polymer-bound sulfonic acid catalyst at temperatures of 60° C. or less and a pressure of from about 0.5 to about 5 atmospheres, and then
  (5) fractionating the resulting mixture to separate 2,5-xylenol from the other components in the debutylation mixture.

7. A method as described in claim 6 wherein the temperature is from about 30° C. to about 50° C.

8. A method as described in claim 7 wherein the selective debutylation is carried out in a continuous reactor containing a suitable polymer-bound sulfonic acid catalyst at a liquid hourly space velocity of from about 0.4 to about 2.5.

9. A method as described in claim 7 wherein the polymer-bound sulfonic acid catalyst is a strongly acidic sulfonated divinylbenzene-styrene copolymer having at least 2% crosslinking.

* * * * *